United States Patent
Nygren et al.

(12)

(10) Patent No.: US 6,783,938 B2
(45) Date of Patent: Aug. 31, 2004

(54) DEVICES FOR OPTICAL DETECTION OF NUCLEIC ACID HYBRIDIZATION

(75) Inventors: Hakan Nygren, Billdal (SE); Manne Johan E. Stenberg, Gothenburg (SE)

(73) Assignee: Biostar, Inc., Boulder, CO (US)

( * ) Notice: Subject to any disclaimer, the term of this patent is extended or adjusted under 35 U.S.C. 154(b) by 14 days.

(21) Appl. No.: 09/982,658

(22) Filed: Oct. 18, 2001

(65) Prior Publication Data

US 2002/0192664 A1 Dec. 19, 2002

Related U.S. Application Data

(63) Continuation of application No. 09/425,072, filed on Oct. 21, 1999, now Pat. No. 6,355,429, which is a continuation of application No. 08/375,151, filed on Jan. 17, 1995, now Pat. No. 6,060,237, which is a continuation-in-part of application No. 07/965,661, filed on Sep. 17, 1992, now abandoned, which is a continuation-in-part of application No. 07/260,317, filed on Oct. 20, 1988, now abandoned, which is a continuation-in-part of application No. 06/832,682, filed on Feb. 25, 1986, now abandoned.

(30) Foreign Application Priority Data

Feb. 26, 1985 (DE) .......................................... 35 06 703

(51) Int. Cl.[7] .............................. C12Q 1/68; G01J 4/00
(52) U.S. Cl. ..................... 435/6; 435/287.2; 435/288.7; 436/164; 436/172; 356/364; 356/369; 536/23.1
(58) Field of Search ...................... 435/6, 287.2, 288.7; 436/164, 172; 356/364, 369; 536/24.3

(56) References Cited

PUBLICATIONS

York University. Transparent Media, from web site: http://www.yorku.ca/eye/transpar.htm.*
Olympus MIC–D. Digital Microscope Global web site: http://www.mic–d.com/curriculum/lightandcolor/reflection.html.*

* cited by examiner

*Primary Examiner*—Carla Myers
(74) *Attorney, Agent, or Firm*—Foley & Lardner LLP

(57) ABSTRACT

An optical device for determining the presence of a first nucleic acid in a sample comprising a second nucleic acid complementary to the first nucleic acid and able to hybridize with the first nucleic acid under hybridizing conditions, the second nucleic acid being bonded to a solid support, wherein the solid support is formed as a light reflecting surface having a first thickness when bonded to the second nucleic acid, and wherein the light reflecting surface has a second thickness, wherein the first and second nucleic acids are hybridized, and the first and second thicknesses can be distinguished by their effect on the light reflecting properties of said light reflecting surface independent of any label present on the first nucleic acid.

8 Claims, 4 Drawing Sheets

DEVICES FOR OPTICAL DETECTION OF NUCLEIC ACID HYBRIDIZATION

CROSS-REFERENCE TO RELATED PATENT APPLICATIONS

This application is a continuation of application Ser. No. 09/425,072 filed Oct. 21, 1999, now U.S. Pat. No. 6,355,429 which is a continuation of application Ser. No. 08/375,151 filed Jan. 17, 1995, now U.S. Pat. No. 6,060,237 which is a Continuation in part of U.S. application Ser. No. 07/965,661, filed Sep. 17, 1992, now abandoned, which is a continuation of U.S. Ser. No. 07/260,317, filed Oct. 20, 1988, now abandoned, which is a continuation of U.S. Ser. No. 06/832,682, filed Feb. 25, 1986, now abandoned, which is entitled to foreign priority from West German Application No. P3506703.9-52, filed Feb. 26, 1985, entitled "A Method of Sequence Analysis of Nucleic Acids in Particular Deoxyribonucleic Acid (DNA) and Ribonucleic Acid (RNA), As Well As A Support for Performing the Method and A Method for Producing the Support," each of which is hereby incorporated in their entirety herein, including all drawings, tables and claims.

FIELD OF THE INVENTION

The present invention relates generally to fields using devices and methods for detecting nucleic acid hybridization.

BACKGROUND OF THE INVENTION

The following is a discussion of relevant art, none of which is admitted to be prior art to the appended claims.

Nucleic acid probe technology has application in detection of infectious disease and genetic and cancer screening. Nucleic acid based probe methods offer several advantages over conventional microbiological or immunological methods for detection of organisms, as described by Nakamura and Bylund (*J. Clinical Laboratory Analysis*, 6, 73–83, 1992).

Methods to amplify either the number of copies of the nucleic acid available for detection or the signal generated after hybridization of the nucleic acid probe have been utilized. A review of nucleic acid based detection methods and various amplification schemes such as polymerase chain reaction (PCR), ligase chain reaction (LCR), transcription based amplification, cycling probe reaction, Qβ replicase, and strand displacement amplification may be found in M. J. Wolcott, *Clinical Microbiology Reviews*, 5, October 1992, pp 370–386.

U.S. Pat. No. 5,175,270 describes an amplification reagent consisting of layers of nucleotide polymers containing double stranded and single stranded sections. Each section has an end which is capable of hybridizing with another molecule.

Probe or hybridization assays are often based on the attachment of an oligonucleotide probe to a surface in order to capture a target nucleic acid molecule (analyte) from a sample. The attachment of this probe to the surface may be through covalent bonds or through a variety of passive absorption mechanisms (e.g., hydrophobic or ionic interactions).

U.S. Pat. No. 5,279,955 describes an immobilization process which uses a heterofunctional cross-linker for a plastic support. The cross-linker consists of a central ring which is hydrophobic and interacts with the plastic, and a hydrophilic chain which terminates in a group capable of reacting with a nucleic acid. Covalent attachment is achieved through a succinyl-olivetol-N-hydroxysuccinimide.

U.S. Pat. No. 5,262,297 describes immobilization of a probe through co-polymers which contain reactive carboxylic acid groups and an 8–50 atom spacer with two or more unsaturated groups within the spacer.

U.S. Pat. No. 5,034,428 describes an immobilization process for probes in which a monomer is joined onto a hydrophilic solid support which can be irradiated in an oxygen free atmosphere. This method provides for covalent attachment of the probe.

U.S. Pat. No. 4,806,546 also describes an immobilization process for an amide modified nylon. The method relies on an amidine linkage under anhydrous conditions in the presence of an alkylating agent.

Maskos and Southern, 20 Nucleic Acids Research 1679, 1992, describe a linker system for the attachment of a nucleic acid to a glass support. The linker system allows for the chemical synthesis of a strand of nucleic acids on the surface. The primary advantage of the linker is that it is stable to an ammonia treatment which is required in the synthesis of the polynucleotide. A hexaethylene glycol spacer is incorporated into the linker which attaches to the glass through a glycidoxypropyl silane which terminates in a primary hydroxy group. The silane is condensed onto silane groups on a solid support. Additional cross-linking may be obtained by introducing water so that the epoxide group is cleaved to a diol. An acidic solution facilitates this process. The length of the linker may be varied by changing the spacer to ethylene glycol, pentaethylene glycol, etc.

Nucleic acid probes that have hybridized to their target sequence are detected based on various methods that introduce a detectable chemiluminscent, fluorescent or other identifiable label into a nucleic acid probe. Several of these techniques are described in U.S. Pat. Nos. 4,968,602, 4,818, 680, 5,104,791, and 5,272,056, and International applications WO91/00926 and GB2169403A.

Arnold et al., U.S. Pat. No. 5,283,174 describe the use of a chemiluminscent label with DNA probes. The label is composed of an acridinium ester and has a number of desirable properties. It is stable to hybridization conditions, light is emitted only upon exposure to an alkaline peroxide, the emission kinetics are rapid, and the label on the unhybridized probe can be destroyed without an impact on the signal generated by hybridized probe.

U.S. Pat. No. 5,089,387 describes a diffraction assay for the detection of DNA hybridization. In this invention, a solid support, generally silicon or poly-silicon, is coated with a DNA probe. These surfaces are required to inherently adhere the DNA probe to the surface. Once the surface is coated with the probe, the surface is selectively inactivated to provide a series of very strictly controlled reactive probe lines for the generation of the diffraction grating. The unreacted surface is required to be non-light disturbing. The diffraction grating is only generated upon the addition of the analyte to the surface. The angle of diffraction is a function of the wavelength of incident light and the density and spacing of the individual gratings on the surface. A single detector or a multiple detector array may be used to detect and measure the light from all desired orders of the diffracted light.

Mixed phase systems have typically been used to perform hybridization assays. In mixed phase assays the hybridizations are performed on a solid phase such as nylon or nitrocellulose membranes. For example, the assays usually involve loading a membrane with a sample, denaturing the DNA or creating single stranded molecules, fixing the DNA or RNA to the membrane, and saturating the remaining membrane attachment sites with heterologous nucleic acids to prevent the probe reagent from adhering to the membrane in a non-specific manner. All of these steps must be carried out before performing the actual hybridization.

SUMMARY OF THE INVENTION

This invention features improved devices, and methods for producing and using optical devices, for detecting the presence or amount of a specific target nucleic acid within a sample. The current invention is based on a probe coated substrate which is optically active. Surfaces can be preselected for the type of optical thin film detection to be employed, and enable direct detection of the hybridization reaction through the interaction of light with thin films. Detection of specific target nucleic acid sequences is also referred to as sequence analysis.

This invention also describes materials and methods for producing optically active solid supports or devices for use in nucleic acid hybridization assays and immobilization of nucleic acid probes to such surfaces.

These surfaces are compatible with a wide range of optical thin film detection methods, all of which utilize some interaction of thin films with light. Such optical thin film detection methods include optical interference, ellipsometry—comparison, null, photometric and other modifications, attenuation of polarized light at non-Brewster angles, profilometry, scanning tunneling microscopy, surface plasmon resonance, evanescent wave techniques, reflectometry, or atomic force microscopy.

The direct optical thin film detection methods of the current invention are extremely sensitive to changes in mass at the surface of an optically active substrate. These optical thin film detection methods provide increased sensitivity for hybridization assays without the introduction of signal generating labels or pre-assay target amplification with its accompanying complexity and limitations. Thus, assay protocols utilizing optical thin film detection methods are greatly simplified, are more rapid, and less costly than conventional indirect assay methods. Total assay times may vary from one hour to a few minutes from the initiation of the assay protocol (ie., from the time that the target nucleic acid containing sample is contacted with the device). Such devices also allow for assay results to be visualized as a color change or detected by instrumented formats.

The methods and devices of the claimed invention by concentrating on improving characteristics of the surface immobilized probe and detection of the hybridization reaction without the use of a labelled component allow for rapid, convenient, and sensitive assays for diagnostic (routine clinical) and research use.

In a first aspect the invention features an optical assay device for detecting the presence or amount of a target nucleic acid. The device includes an optically active substrate capable of producing a thin film effect, and exhibiting a first set of reflective and transmissive properties in response to light impinging thereon, and exhibiting a second set of reflective and transmissive properties different from said first set, in response to light when the target nucleic acid is bound to a target specific capture probe and creates a change in mass on said optically active substrate. The target specific capture probe is attached to an attachment layer that is present on the optically active layer. Detection of the second set of reflective or transmissive properties indicates the presence or amount of the target nucleic acid.

An "optically active substrate" comprises an optically active surface. Such a substrate may consist of more than one layer (multi-layered), for example; base material, a conducting metal layer of aluminum, chromium, or a transparent conducting oxide, and a layer of amorphous silicon, wherein the metal layer is positioned adjacent the amorphous silicon. Alternatively, the multi-layered substrate may comprise a layer of base material (any solid material on which optically active layers may be applied), and a layer of amorphous silicon adjacent the base material. The base material is selected from any of the group consisting of glass, fused silica, plastics, semiconductors, ceramics, and metals, and may be either rigid or flexible. The optically active surface substrate also serves as a solid support for the nucleic acid target probe and any amplification components (if necessary) and must be chemically stable to the application of the attachment layer, the nucleic acid probe, and all assay reagents. The properties of the optically active substrate are matched to the direct optical thin film detection method employed.

An "optically active surface" is a surface that participates in the generation of an optical effect such that the light impinging upon that surface is in some way altered. Such optically active surfaces may be adapted to respond not only to polychromatic light (e.g., white light) but also to monochromatic light (e.g., laser light, which may be inherently polarized). The optically active surface may be designed to reflect or transmit light. The substrate may inherently possess an optically active surface or the substrate may require an optically active surface be applied to introduce the desired optical characteristics. Thus, the optically active substrate may inherently possess the properties required for a given thin film detection method, or a surface may be modified to provide the required optical properties. Materials which are suitable for optically active substrates include monocrystalline or polycrystalline silicon, glasses, ceramics, metals, amorphous silicon on glass, amorphous silicon on plastic, plastics, and composites of these materials.

By "thin film effect" is meant that light impinging on an optically active surface or substrate is attenuated or modulated in its reflective or transmissive properties.

The first set of reflective or transmissive properties is defined as a combination of wavelengths of light, or a spectral distribution, or an intensity of one or more of wavelengths, or a degree or amount of elliptical polarization, or an amount of polarization rotation. The substrate also exhibits a second set of reflective or transmissive properties which is different from the first set. The second set of reflective or transmissive properties is exhibited in response to the same light when the target nucleic acid is present on the surface. This second set of reflective or transmissive properties is due to a change in mass on the optically active substrate. The change from one set of properties to another can be measured either by use of an instrument, or by eye. The optical active substrate is selected to be compatible with the method of optical thin film detection.

The target nucleic acid is selected so that it specifically identifies a single organism or gene. The target sequence is selected such that the stringency of the assay conditions will promote or enhance the specificity of the assay. The target nucleic acid may be a DNA or RNA (rRNA, tRNA, mRNA, small nuclear RNA's (SNURPS)) molecule either intact or a fragment thereof covering a range of molecular weights. Fragments may be generated enzymatically, chemically, or by mechanical shearing. The target may be free or contained within a larger complex, i.e., complexed with protein(s). The target may be single or double stranded oligonucleotide and the source may be a bacterium, a virus, a human cell, and may be isolated from a culture medium or a biological fluid.

A "target specific capture probe" refers to a synthetic or biologically produced nucleic acid which by design contains specific, complimentary nucleotide sequences that allow it to hybridize to a target nucleic acid sequence. The probe may be composed of deoxyribose, ribose, or a combination of these nucleotides (chimera) and may be synthesized chemically, isolated from a biological source, or cloned. It may be a linear strand or may contain branch points to increase the density of immobilized probe. The probe may provide a single or multiple copies of the sequence complimentary to the target nucleic acid. The nucleic acid probe or capture probe is selected to specifically hybridize a target nucleic acid. When more than one probe is used in a hybridization assay, each probe should recognize a unique sequence well separated from each other within the target oligonucleotide.

Hybridization is the process by which two partially or completely complementary strands of nucleic acid are allowed to come together, under predetermined reaction conditions, in an antiparallel fashion to form double stranded nucleic acid with specific and stable hydrogen bonds. The nucleic acid capture probe sequence is selected to specifically interact with the target molecule or analyte at a pre-determined degree of stringency. The probe length is pre-determined to provide the required specificity at the degree of stringency used in the assay. Assay conditions are set so that the stringency of hybridization between the capture probe and the target nucleic acid provides the required specificity.

Stringency of a particular set of hybridization conditions is defined by the length and base composition of the probe/target duplex as well as by the amount and geometry of mispairing between the two nucleic acids. It is governed by such solution parameters as concentration and type of ionic species, type and concentration of denaturing agents, precipitating agents, and the temperature of hybridization. As stringency increases, longer probes are preferred for the generation of stable hybrids. The stringency of the reaction conditions control the specificity of a hybridization assay. For a complete review of hybridization assay conditions see "Molecular Cloning—A Laboratory Manual", second edition, Sambrook, Fritisch, and Maniatis. Also, software has been developed that can more accurately predict hybridization conditions than these traditional methods.

The capture probe may be modified to promote passive adhesion to the attachment layer or be chemically reactive with other surface immobilized materials to allow covalent attachment. The modifications should be made to the sugar-phosphate backbone to prevent stearic problems associated with attachment at the bases. A linker may be introduced into the probe sequence to space the probe from the surface and facilitate attachment.

It is critical that the probe on the surface be attached so that the individual monomers are free to hybridize with the target without stearic inhibition. This may be particularly relevant when simple hydrophobic interactions are used to immobilize the probe because base interactions will be blocked. Covalent methods of attachment can eliminate these considerations and also improve the efficiency and kinetics of hybridization. A determination of the correct position for probe attachment (horizontal or end) may be made empirically. In addition, covalent attachment of the probe should not block additional binding sites on the surface. Thus, the probe surface density will not be reduced. Covalent attachment techniques which modify any or all of the probe nucleotide residues must be avoided as they could impact subsequent hybridization reactions.

By "mass change" is meant a modification (increase or decrease) in the amount of material at the surface of an optically active substrate such that one or more of the reflective and/or transmissive properties of the optically active substrate are altered.

In many cases the optically active substrate selected in conjunction with a specific optical detector is not readily reactive nor will it retain the nucleic acid probe. Thus, the surface must be modified with a material which enhances or assists in the immobilization of the probe onto the optical substrate. These materials are referred to as attachment layers. The materials selected for the attachment layer must provide the following characteristics.

Attachment layers must react either in a covalent or very strong non-covalent manner with the optical substrate. The probe may be adhered to the attachment layer either covalently or passively. The attachment layer may be activated to react with the probe, the probe may be activated to react with the attachment layer, or both may be chemically activated to react with each other. The attachment layer can be selected to determine the type of interaction (hydrophobic, hydrophilic, ionic, hydrogen bonded) which occurs between itself and the capture probe. Attachment layers may be applied to the surface of the optical substrate by spin coating, solution coating, vapor deposition, spray coating or the like. The layer must be applied in a uniform fashion from a solvent system which will not damage the optical substrate or the chemical properties of the attachment layer. Ideally, the solvent will volatilize from the surface film during the final curing process.

In a preferred embodiment the invention features a device with an amplifying probe reagent able to bind to the target nucleic acid and create an increase in mass change on the optically active layer, without disrupting the thin film effect, when the target nucleic acid is bound to the target specific capture probe.

An "amplifying probe reagent" is designed to increase the mass of the immobilized target nucleic acid on the optically active substrate. This amplification may be required to increase the sensitivity of the hybridization assay in the optical thin film detection system. The amplifying probes are attached to another catalytic component or particle which will increase the mass when the target nucleic acid is captured on the surface. The only requirement for such a material is that it can be tightly associated with the amplifying probe and that the resulting mass deposited at the surface not disrupt the thin film effect. When a catalytic component is attached to the signal amplifying probe, or amplifying probe, it may act on yet another material, further increasing mass on the optical substrate. There may be a surface immobilized capture probe and one or more signal amplifying probes.

By "increase in mass" is meant that the mass change produced is greater than that produced by the binding of the target nucleic acid.

By "without disrupting the thin film effect" is meant that the optical effect generated by light impinging on the optically active substrate is not destroyed by the introduction of additional materials to the surface of the substrate. For example, materials which would scatter light are disruptive to a thin film interference or other reflective techniques, as they would artificially reduce the signal available to a detector.

In further preferred embodiments the amplifying probe reagent comprises a target specific nucleic acid sequence and a catalytic component or a particle; the catalytic component is capable of interacting with additional materials to increase the mass change and result in a second set reflective and transmissive properties without disrupting the thin film effect; the catalytic component is an enzyme; and the particle is selected from the group consisting of metallic particles, silica particles, and film forming latexes.

By "catalytic component" is meant any material which can interact with a substrate to create an insoluble product. Examples of these materials include enzymes, metals and other components which cause a reaction to occur faster than it would occur in the absence of that material.

By "particle" is meant a material such as a film forming latex or small non-scattering metal or glass particles.

By "additional materials" is meant an assay component which is specifically modified by the catalytic component to produce a precipitating material. The precipitating agent may be a substrate for an enzyme, e.g., containing 3,3',5,5'-tetramethylbenzidene when the enzyme conjugate has an immobilized peroxidase or the precipitating agent is a substrate containing 5-bromo-4-chloro-3-indolyl phosphate when the conjugate is alkaline phosphatase.

The following preferred embodiments are applicable to the device with and without the use of an amplifying probe reagent. The attachment layer is selected from the group consisting of polymeric siloxanes, mixtures of polymeric siloxanes, film forming latexes, and silyl modified nucleotides.

The optically active substrate is selected from the group consisting of silicon, glass, amorphous silicon, plastic, metals, amorphous silicon on glass, amorphous silicon on plastic, and composites of these materials.

An anti-reflective film may be provided between the optically active substrate and the attachment layer. This film which may be formed from silicon nitride, silicon oxides, titanium dioxide, silicon oxynitride or cadmium sulfide and the like. This film acts to cause incident light to undergo interference such that a specific color is produced on the surface of the substrate. This film interacts with other layers on the substrate to ensure that a color change or wavelength intensity change is observed when the target nucleic acid is present on the device.

In a preferred embodiment the anti-reflective film is selected from the group consisting of silicon nitride, composites of silicon and silicon oxides, titanium dioxide, titanates, silicon carbide, diamond, and cadmium sulfide.

In a further preferred embodiment detection is by an optical thin film detection method selected from the group consisting of ellipsometry, optical interference, attenuation of polarized light at non-Brewster angles, profilometry, reflectometry, scanning tunneling microscopy, atomic force microscopy, surface plasmon resonance, evanescent wave techniques, interference spectroscopy, and various other forms or combinations of polarimetry, reflectometry, spectroscopy, and microscopy. This invention concerns the application of such technologies for the direct detection or measurement of changes in the thickness, density, refractive index, optical thickness, or mass of thin films resulting from the concentration-dependent immobilization of target nucleic acid on a surface coated with a suitably selected probe. All these properties maybe applicable when a thickness or mass change occurs. Such thin film assay-technologies directly detect or quantitate the material of interest, and are alternatives to conventional solid phase assays.

In other preferred embodiments the first and second set of reflective or transmissive properties are visual interference colors; the first and second set of reflective or transmissive properties are changes in the degree of rotation observed in polarized light; the first and second set of reflective or transmissive properties are changes in the ellipticity of the impinging polarized light.

By "visual interference colors" is meant the change in interference colors produced by modifying an anti-reflective layer.

By "degree of rotation observed in polarized light" is meant the attenuation of the degree or amount of rotation measured in polarized light incident upon the optically active substrate before and after reaction with the target molecule as measured by a change in intensity of the incident light.

By "changes in ellipticity of the impinging polarized light" is meant the attenuation of the ellipticity measured in polarized light incident upon the optically active substrate before and after reaction with the target molecule as measured by a change in intensity of the incident light.

In additional preferred embodiments the target nucleic acid is DNA, rRNA, mRNA, tRNA, small nuclear RNA, or complexes of said nucleic acid with other materials; the target nucleic acid is single stranded or double stranded; the target nucleic acid is obtained from a bacterium, a virus, a human cell, a culture, serum, plasma, blood, urine, sputum, tissue sample, or other biological fluid. Target nucleic acid is obtained from a source by the use of routine extraction and isolation procedures familiar to those who practice the art. The target nucleic acid may also require denaturation to allow for hybridization with the capture probe, such procedures are also standard in the art.

In a further preferred embodiment, the capture probe is a synthetic or biologically produced nucleic acid which may consist of DNA, RNA, or a chimeral the capture probe is a linear strand providing single or multiple copies of a sequence complimentary to the target nucleic acid; the capture probe is a branched, multi-copy sequence complimentary to the target nucleic acid; the capture probe is adhered to the attachment layer by hydrophobic interactions; the capture probe is adhered to the attachment layer by hydrophilic interactions; the capture probe is adhered to the attachment layer by ionic interactions; the capture probe is adhered to the attachment layer by hydrogen bonding; the attachment layer comprises a film forming latex and the capture probe is a chimeric probe which is covalently attached to the attachment layer.

By "chimera" is meant that the capture probe consists of both DNA and RNA. For example, a single ribonucleotide maybe incorporated into a DNA capture probe and is used in covalent attachment of the capture probe to the optically active surface. The ribonucleotide residue may be treated with an oxidizing agent such as periodate to produce a dialdehyde which is reactive with a carbonyl hydrazide modified surface. A covalent modification of the optically active substrate is produced.

By "branched multi-copy sequence" is meant a probe with a branch point such that from emanating branches a copy of the specific capture sequence is extended, thus presenting multiple copies of the capture probe.

In a second embodiment the invention features a method for detecting the presence or amount of a target nucleic acid. The method consists of: preparing a sample, potentially containing a target nucleic acid, for hybridization, contacting the sample with a capture probe supported on an optically active substrate under conditions such that the probe specifically hybridizes to the target, and determining the amount or presence of the target on the optically active substrate by an optical thin film detection method.

By "preparing a sample" is meant treatment of a sample so that a target nucleic acid is in a condition that would allow for hybridization with a capture probe and includes extraction and isolation procedures known to those skilled in the art.

In a preferred embodiment the target nucleic acid after being bound to the capture probe is contacted with an amplifying probe reagent.

In a third embodiment, the invention features a method for increasing capture probe density whereby the probe is applied to an attachment layer on an optically active substrate by spin coating. The density of the immobilized probe is increased by this process relative to a conventional solution coating process.

By "capture probe density" is meant the amount of capture probe available to bind the target nucleic acid s or the number of capture probes per specific amount of surface area.

By "spin coating" is meant the standard semiconductor coating procedure.

In a fourth aspect, the invention features a kit for an optical assay for a target nucleic acid having a test device with an optically active substrate with an attached capture probe which is reactive with the target nucleic acid, and a reagent adapted to react with the target bound to the surface to alter the mass on the surface. Preferably, the reagent is an enzyme conjugate or a polymeric film forming latex.

The kit comprises an optically active substrate coated with a target specific capture probe. The kit may contain reagents for the extraction of the target oligonucleotide from a biological sample, reagents to destabilize the initial target duplex or other secondary structure, hybridization reagents, stringency washes, sample processing tubes and transfer pipettes, and amplifying reagents if required.

In a fifth embodiment the invention features an optical assay device for detecting the presence or amount of a target nucleic acid comprising: an optically active substrate exhibiting a first set of reflective properties in response to light impinging thereon, and exhibiting a second set of reflective properties different from the first set, in response to the light when the target nucleic acid is bound to a target specific capture probe so as to result in a mass change on the optically active substrate. The target specific capture probe attached to said optically active substrate, and detection of said second set of reflective properties indicates the presence or amount of said target nucleic acid.

Other features and advantages of the invention will be apparent from the following description of the preferred embodiments thereof, and from the claims.

DESCRIPTION OF THE PREFERRED EMBODIMENTS

Figure 1:
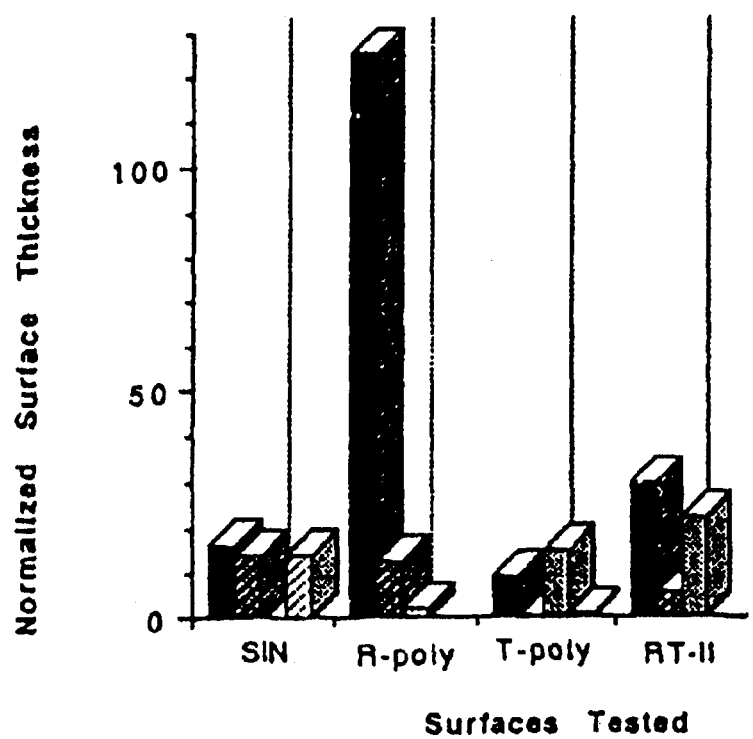
FIG. 1 is a chart comparing the amount of HRP/TMB precipitation on various attachment surfaces coated with biotinylated DNA. Solid rectangles represent DNA and conjugate. Darkly stippled rectangles represent conjugate only. Lightly stippled rectangles represent DNA only. Striped rectangles represent no DNA and no conjugate. The y axis represents thickness in angstroms normalized to the substrate thickness. The x axis represents the various attachment chemistries.

The following descriptions are for further illustrating the various embodiments of the present invention and are in not intended to be limiting in scope.

The first component required is the optically active substrate. The substrate may be intrinsically optically active or modified to provide the appropriate properties for the detection method selected. Detection methods described include a visual interference assay and numerous instrumented systems including ellipsometry-comparison, null, photometric and other modifications, attenuation of polarized light at non-Brewster angles, profilometry, scanning tunneling microscopy, surface plasmon resonance, evanescent wave techniques, or atomic force microscopy.

This invention is suited to use of a variety of optically active substrate materials and formats based on the needs of the end user. The optically active substrate can be formed of, or have coated on it, a material that provides either diffuse or specular reflection, it may be rigid or flexible, reflective or transmissive. Devices designed for instrumented analysis do not require an anti-reflective (optical thin film) coating on the substrate, while those designed for viewing by eye require such a coating. Criteria useful for selecting an optical substrate for instrumented applications, or for viewing by eye of a color-signal generating application, are presented below.

A wide range of rigid materials may form the optically active substrate, including glass, silicon, fused silica, plastic, ceramic, metal, and semiconductor materials. The substrate may be of any thickness desired. Flexible optical substrates include thin sheets of plastic and like materials. Most substrates require only a standard solvent, plasma etching, or acid cleaning, well known S to those skilled in the art, before subsequent layers may be deposited on them.

The surfaces of many solid materials, such as glass, and semiconductor materials, such as silicon, metals, etc., are sufficiently smooth to provide specular reflection if they are polished. For use in a reflection-based assay the major requirement in selecting an optical substrate is that the reflection occur, or be made to occur, only at the upper surface. This is especially critical for devices which include an interference film IS which are viewed by eye. This is accomplished by vapor deposition of a thin metal film on the substrate, and attachment of subsequent optical layers by techniques known to those skilled in the art. For example, the uppermost surface of a glass substrate may be coated with a layer (amorphous silicon) to prevent unwanted reflections from the lower surface.

If the substrate is to be used in a reflection mode, and is partially or fully transparent, it may be coated with an opaque material to block transmitted light and allow reflection to occur only from the upper surface. For example, a glass substrate may be coated with a layer of aluminum, chromium, or other transparent conducting oxide, by mounting in a vacuum chamber facing an aluminum-filled tungsten boat. The chamber is evacuated to a pressure of $1 \times 10^{-5}$ Torr. Current is passed through the tungsten boat, raising it to a temperature at which the aluminum deposits on the substrate at a rate of 20 Å/second for 100 seconds, coating the glass with an opaque layer of aluminum having a thickness of 2000 Å. Thinner layers of aluminum or chromium may also be used to eliminate any back surface reflections. Non-conducting deposition techniques may be used to deposit the metal film.

The aluminum-coated glass, described above, may be considered optically passive. Thus, if it is coated with a layer of hydrogenated amorphous silicon (a-Si:H), the optical characteristics of the substrate will be derived from the a-Si:H alone. The aluminum-coated glass is required only when the amorphous silicon deposition process requires a conducting surface. Techniques which do not require the use of a conducting surface for the deposition of amorphous silicon are known. To produce this substrate, the aluminum-coated glass is mounted on one of two opposing electrodes in plasma-enhanced chemical vapor deposition system. The system is evacuated, and the substrates are heated to 250° C. A constant flow of silane ($SiH_4$) gas into the chamber raises the pressure to 0.5 Torr. A plasma is struck by applying 10 $mW/cm^2$ of RF power to the electrodes. A film of a-Si:H deposits on the substrates, and grows to a thickness of approximately 1000 nm in about 75 minutes. The a-Si:H so formed may form the first optically functional layer on the test surface.

A glass substrate coated only with a-Si:H (without the aluminum layer), is also useful in this invention. Transparent substrates, such as glass, fused silica, sapphire, and many plastics may be used in instrument transmission measurements, without additional modification. Color-signal generation visible to the eye is possible with a transmissive substrate where the anti-reflection properties of the coatings are determined from the transmitted light.

In one example, the optical substrate is formed from a silicon crystal which is grown and extruded to 4 inches in diameter and then diamond sawed to form a wafer. The wafers are treated with chemical etchants to smooth the surface and reduce flaws. The wafers are lapped or ground with aluminum oxide, titanium oxide, or silicon carbide particles in a talc slurry. The initial grain size is large and successively smaller particle sizes are used to produce an increasingly smoother surface. Both sides of the wafer are subjected to this process. The final lapping process leaves a very diffusely reflective surface. Wafers may be further processed with chemical or plasma etching to modify the diffuse reflecting characteristic of the substrate. Once the wafers are lapped, they are cleaned using the following process or a known modification thereof: the wafers are sonically cleaned with a cationic detergent, followed by a rinse with 18 megaohm water. Then they are cleaned with an anionic detergent, followed by a rinse in 18 megaohm water. They are ultrasonically cleaned with an aqueous ammonia solution made of 370 ml of 30% $H_2O_2$, 250 ml of aqueous ammonia and 9 gallons of water, and are rinsed in a cascade of water with the final rinse being with 0.1 micron filtered water. They are then spin-dried and are ready for optical coating. An alternative to this procedure is the "NRCA Clean" described in Polymer Surfaces and Interfaces, edited by W. J. Feast and H. S. Munro, John Wiley and Sons, N.Y., N.Y., page 212, 1987.

The substrate material may be cut, sawed, scribed, laser scribed, or otherwise manipulated into the desired test piece configuration. Suitable test pieces for a single use assay are 0.5 $cm^2$ to 1 $cm^2$ with 0.75 $cm^2$ being preferred. Test piece sizes are not restricted to the above, as alternative formats may require substantially more or less reactive test surface.

For the color-signal generation methods only, substrate selection will determine the characteristics of the anti-reflective material or materials used in subsequent coating steps. The simplest description of a single optical thin film is that the substrate is coated with a thin layer of material such that reflections from the outer surface of the film and the outer surface of the substrate cancel each other by destructive interference. Two requirements exist for exact cancellation of reflected light waves. First, the reflections must be 1800 out of phase and, second, they must be of equal amplitude or intensity.

In the reflection mode, the optical thin film properties of the coatings of a device of this invention suppress the reflection of some wavelengths of light and enhance the reflection of others. This causes the suppressed wavelengths of incident light to enter the substrate, or an opaque coating on the substrate where they are absorbed. Most of the light of other wavelengths, whose reflection is not suppressed, does not enter the coated substrate and is reflected, however, some components may be absorbed. As the optical thickness of the coating changes, the range of wavelengths in the reflected light changes. In transmission mode, the properties of the coatings suppress the reflection of some wavelengths of light and enhance the reflection of others, as in the reflection mode. This causes the suppressed wavelengths of the incident light to enter the substrate and to be transmitted. Light of other wavelengths, whose reflection is not suppressed to as great an extent is reflected, and transmitted to a lesser extent. As the optical thickness of the coating changes, the range of wavelengths in the transmitted light changes.

Where visible signal generation is required, the final assay result may also be measured by instrumentation. Ideally, for the production of a perfect interference film using only the a nucleic acid probe, and an optical substrate, the substrate should have an approximate refractive index of the square of the refractive index of the receptor layer (see below), i.e., $(1.5)^2$ or 2.25 (variations in this number can still provide useful devices of this invention). The material selected should be mechanically stable to subsequent processes, reflective, and of known refractive index. It is not always possible to match the optical substrate to a particular film, for example, a biological film. In these cases, an intermediate optical thin film must be used to compensate for the lack of a suitable optical substrate. For eye-visible color-signal generation, the substrate material is subject to two restrictions: first, it must adhere to the optical thin film material, and second, in the simplest case, the refractive index of the substrate should approximately equal the square of the refractive index of the material directly above it or, on a more complex test surface, the refractive index of the substrate should be selected to fit generally one of the formulae in Table 3, pp 8-48 to 8-49, of the "Handbook of optics". For example, use of a silicon wafer with a refractive index of approximately 4.1 allows a test surface to be designed with a wide variety of corresponding optical thin films or anti-reflective materials. The material should be coated to a thickness of a quarterwave for the wavelengths to be attenuated, or variations in the formulae. Those skilled in the art will realize that various other substrate materials are equally suited for use as a test surface if they satisfy the above criteria.

The optical thin film coating is deposited onto the surface of the substrate by known coating techniques; for example, by sputtering or by vapor phase deposition in a vacuum chamber. Various other useful coating techniques are known to those skilled in the art. Materials useful as optical thin film coatings are formed of clear material which is significantly transmissive at the thickness utilized, and suppresses some wavelength of reflective light when coated onto the substrate. The film, once deposited onto the optical substrate, is also stable to subsequent processes.

Preferably this test surface will have fewer optical layers, but more complex test surfaces possessing more layers corresponding to the known formulae. As already noted, the theoretical calculations are the starting point for material selection. Theoretical considerations may be used to determine which materials are compatible with a pre-selected substrate. The coating thickness may be set at the predetermined quarterwave thickness or to a preselected interference color. However, for the construction of a probe/optical thin film composite of this invention a number of adjustments are required to the initial optical thin film coating. An empirical optimization scheme is detailed below.

A model was developed to select an optimal background interference color for any particular combination of substrate, optical thin film (AR film), attachment layer and nucleic acid probe. Since the mathematical models developed to date are not effective to provide useful devices of the present invention, these models are used only as a starting point in the device construction. Optimization is necessary to provide a device of this invention. For illustration purposes only, the selected substrate was a silicon wafer and the optical material selected was silicon nitride. The most highly contrasting colors observed were a yellow-gold changing to magenta with an increase in mass on the test surface.

A method for selection of the optimal thicknesses of each layer for a device of the present invention is disclosed for a silicon nitride film on silicon. In step 1, a silicon substrate is provided either with a specular or non-specular surface. A silicon nitride film is provided on this surface in steps 2 and in step 3, this film is eroded away in a stepwise fashion by heating and stirring in an appropriate solution. The timing of each step is selected such that the portion which is subjected to erosion for the longest period of time exhibits a pale gold color, while that portion which is not exposed to erosion exhibits a deep blue color. In steps 5 and 6 respectively, an attachment layer and a receptive material layer for the target nucleic acid to be detected are provided on the silicon nitride. These layers are provided in a thickness which may be determined empirically, or can be similarly optimized (e.g., in this stepwise fashion) if so desired. In step 7, an assay is performed with three portions of the strip being treated in a different manner such that a negative response, a weak response, and a strong response can be recorded. The thickness of silicon nitride useful in the invention can be determined by those sections providing the strongest weak positive response in the test while maintaining a clean negative response.

Specifically, a silicon wafer was prepared with a thick coating (800 Å) of silicon nitride so that the wafer appeared to be a deep blue. Then the optical thin film material was etched off the wafer in a hot, phosphoric acid bath to produce a wedge of interference colors. The optical material was etched such that 300 Å remained at one end of the wedge and 700 Å remained at the other end of the wedge. (At 100° C. the silicon nitride was removed at approximately 20 Å per minute.) The optimal film thickness is most readily selected based on the composite test surface analysis. This process maximizes the visual contrast obtained for the specific assay under development.

Silicon nitride is easily etched to produce the wedge of thicknesses needed for this empirical evaluation.

Many materials are susceptible to an acid or base etching processes. Other chemical methods of etching materials are known. If a desired optical film is not easily removed from a particular optical substrate because the film is too easily destroyed, or the optical substrate is not stable to the required etchant, another method of generating the wedge may be used. For instance, monocrystalline silicon is not stable to prolonged exposure to basic solutions. If an optical film on silicon requires a basic etchant the wedge can not be generated using a chemical approach.

Several alternatives exist; first, the optical film may be deposited on an optical substrate which is introduced stepwise into the coating chamber over a period of time. Each newly exposed section will receive a thinner coating than the previously exposed section. Second, the substrate may be masked and the mask removed stepwise over a period of time. Third, several different coating runs each producing a different thickness of optical material may be performed. Fourth, ion milling may also be used to etch certain materials. For any given optical substrate and substitute optical thin film, of the same refractive index as the original optimized optical thin film, the process need not be repeated. Minor thickness adjustments may be required if the refractive index is not exactly that of the original material.

Thus, the formulae established for the coating of optical thin films are used as a guideline only for the production of a test surface suited to a specific binding assay. For a pre-selected substrate, the square root dependence of an optical thin film is used to screen appropriate optical materials. Some deviation from the perfect square root dependence is acceptable for this invention. The use of a quarterwave thickness of the optical coating is only an initial guide to coating thickness. Thickness of the optical thin film must thus be empirically derived in consideration of the nucleic acid capture probe. The composite of the nucleic acid capture probe and the optical thin film of this invention does not meet the conditions theoretically required to produce such a film. Neither the thickness nor the refractive index rules are followed. Surprisingly such deviation from these accepted formulae results in a test surface which is very sensitive to mass changes or thickness changes.

While of less importance, the relative thicknesses of each layer, and not just the optical thin film layer, may be varied as described above to optimize the final test device for any particular attachment layer and receptive material layer.

Other optical thin film materials that have a similar refractive index include, but are not limited to: tin oxide, zinc oxide, chromium oxide, barium titanate, cadmium sulfide, manganese oxide, lead sulfide, zinc sulfide, zirconium oxide, nickel oxide, aluminum oxide, boron nitride, magnesium fluoride, iron oxide, silicon oxynitride ($Si_xO_yN_z$), boron oxide, lithium fluoride, and titanium oxide.

After substrate selection, an appropriate attachment layer must be applied to allow the immobilization of the capture probe. The capture probe may be immobilized by passive adhesion to the surface or through covalent methods. While stearic availability of the nucleic acid bases for hybridization is one consideration, especially for the planar substrates of this invention, another is the density of capture probe on the surface. An optically active substrate can be derivatized with a number of different attachment polymer types. The attachment layer can be used to control the hydrophobicity/hydrophilicity of the surface and thus affect the density and availability of the capture probe. An attachment layer must be stable under the conditions used to attach the capture probe to the surface and to subsequent washes. The methods of applying a variety of attachment layers to an optical substrate are provided in the examples below. The composition of the attachment layer will determine the mode of immobilization for the capture probe.

In a preferred embodiment, the attachment layer is spin coated or aerosol spray coated in a uniform manner. The various intermediate materials are coated to the substrate at thicknesses between 5 Å and 500 Å (thicker amounts can be employed). The layer can be formed of any material that performs the following functions and has the following characteristics; creates a favorable environment for the capture probe, permits the probe to be bound in active, functional levels (preferably by a cost-effective method), adheres tightly to the optical substrate, and can be coated uniformly.

Ideally, the surface activation technique should provide a covalent modification of the surface for stability while introducing a very dense uniform or conformal film on the surface of the substrate. A strongly adsorbed conformal film without covalent attachment may be adequate. Substrates such as monocrystalline silicon, macroscopically planar, uniform optical glasses, metalized glass and plastic, whether or not coated with an optical layer (i.e., SiO, $SiO_2$, $Si_xN_y$, etc.) have a deficiency of available reactive groups for covalent attachment, but are still useful in this invention. Once applied, the attachment layer should provide an environment which supports the adherence of a probe layer by covalent or adsorptive interactions, that is dense and functional. This attachment layer must be of sufficient thickness to separate the capture probe layer from any toxic effects of the initial optical substrate.

A general method for covalent surface attachment of DNA capture probes has been devised. The capture probe is attached through the 3' end. A chimeric capture probe is designed which includes at least a single ribonucleotide at the 3' end of the deoxyribonucleic acid polymer. For evaluation purposes, the 5' end of the probe is synthesized with a biotinylated residue. In an actual assay the 5' end would not be modified. The ribose sugar ring in the chimeric probe will open to form a dialdehyde in the presence of sodium periodate by cleaving the 2'-3' bond of the sugar residue (*Methods in Enzymology*, Volume LIX, 1979, pp. 172–181, F. Hansske, and F. Cramer) This opened structure may be reacted with a carbonyl hydrazide modified surface to form a condensed six membered ring structure by the interaction of the aldehydes with the surface nitrogen by beta elimination of the 1' and 4' hydrogens.

The capture probe could also be synthesized containing a Psoralen C2 Phosphoramidite which was originally designed to introduce a fluorescent label into a nucleic acid probe. This molecule when photoactivated will cross-link to any available thymine. The psoralen modification would be used to attach the capture probe to the surface. It may be desirable to add a linker between the probe and the Psoralen monomer. It is also important that the probe not contain a TT sequence or they will dimerize upon photoactivation. Probes can be designed with branching spacers using phosphoramidite chemistries including 5'-Branched modifier C3 or C7 and 3' Amino-modifier C3CPG to introduce multiple copies of probe to linkers with single points of attachment. A primary amine modified spacer could be incorporated into the capture probe which could then be reacted with an aldehyde coated surface. Imine formation can be promoted by NHS/carbodiimide chemistries and then may be reduced with $NaBH_4$. If the oxygen in the phosphate groups of the DNA backbone is replaced with a sulfur group, then coordination complexes with metal surfaces can be used to immobilize the probe.

One of the best approaches for the generation of a long oligonucleotide on the surface is to immobilize an oligonucleotide on the surface then ligate the remaining sequence onto the surface using a ligase reaction. This could be used to covalently attach a probe which contains a large number of repeats of the desired sequence. This would increase the efficiency of the capture of the target by improving the stearic availability of the probe for hybridization.

A hydrophobic surface may be used to immobilize a capture probe which is modified with a poly T tail. A poly T tail is very hydrophobic and can be used to associate with the surface and drive the attachment of the probe to the surface. When this approach is used, samples should be treated to remove poly A tails which would associate with the surface and block the desired hybridization reaction. Alternatively a poly T probe could be used to isolate an mRNA and then specifically identify the mRNA through an amplifying probe.

A carbonyl hydrazide surface may be generated by applying a thin film of a carboxylate modified polymer (such as a film forming latex) to the surface by aerosol, spin coating, dip coating, etc. The carboxylate is then treated with N-hydroxysuccinimide and a carbodiimide followed by hydrazine to create the hydrazide surface. It is also possible to use an amine modified surface for direct interaction with the aldehyde groups.

A capture probe may be modified with a free thiol group at the 3' or 5' end. This free thiol may be reacted with a surface thiol to from a disulfide bond and thus link the probe to the surface. A mercapto siloxane may be used to introduce the thiol onto the surface through a spin coating process. Or a polymer may be combined with a siloxane such as the T-Polymer to create a hydrophobic surface which helps draw the probe to the surface prior to actual attachment. In this case unreacted surface thiols must be blocked prior to subsequent processing, and conditions for the assay must not reduce the dithiol to free thiol groups.

A capture probe may also be linked to a material which is easily adhered non-covalently to the surface. When a surface is coated with the T-polymer, proteins strongly adhere to the solid support. The oligonucleotide is modified at the 5' end with hexanolamine which can be added directly to the probe by a nucleic acid synthesizer. A maleimide is synthesized by the addition of 3-maleimidobenzoic acid in basic solution and purification by anion exchange chromatography. This modified capture probe is then incubated with the protein either in solution or coated onto a solid support to couple the probe and protein. The ratio of the probe: protein and other parameters can be set to control the level of probe incorporation and thus the surface density obtained.

The capture probe must be tightly associated with the surface so as to minimize the rate of removal, especially during the final stringency wash processes. Covalent bonds may be susceptible to heat, changes in ionic strength, and reducing conditions. Non-covalent techniques are susceptible to these conditions and also to the presence of surfactants or other materials which will compete with the mode of attachment used. The bond between the surface and the capture probe must be stronger than the bond between the nucleic acid hybrids to ensure that a high stringency wash does not remove the probe from the solid support.

It was discovered that some of the materials that bound capture probe most-effectively had very little in common; some were very hydrophobic while others were strongly charged. Thus, it is possible to tailor the surface to exploit the amphiphilic nature of the probe and the specific assay application being designed. One type of surface may be well suited to applications were the sample is extensively processed and is primarily a buffered matrix. Another may be best suited to applications where the sample matrix is more closely related to the original biological medium.

Additional materials that could be applied to an optical substrate and serve as attachment layers include hydrophobic isobutyltrimethoxysilane, charged N-trimethoxysilylpropyltri-N-butyl ammonium bromide, composites of these and previously described materials, and crosslinking reagents such as tetramethoxysilane, polystyrene. One interesting silane N-6,9,-bis (trimethylsilyl) adenine could be used to introduce an adenine to the surface for synthesis of the capture probe on the surface or ligation of a capture probe enzymatically to the surface.

In some cases a signal amplifying probe or probes may be required to achieve the sensitivity desired for the detection of the target nucleic acid. As with the capture or immobilized probe, the amplifying probe may be a DNA or RNA probe. The amplifying probe may be modified to include additional mass generating materials. And the oligonucleotide reporter sequence selected should be well separated from the sequence hybridized by the capture probe.

One possible method of signal amplification is to attach the amplifying probe to horseradish peroxidase (HRP) or alkaline phosphatase (AP) and use in combination with a precipitating substrate. See Renz, M., and Kurz, K., "A Colorimetric Method For DNA Hybridization", Nuc. Acids Res., 12, 3435–3444, 1984 for a method to couple an oligonucleotide to these enzymes. Catalytic, but non-enzymatic, reactions which have a specific catalyst and reactant and lead to the formation of an insoluble product may also be utilized. Some mechanism must exist which will allow the attachment of the amplifying probe to the catalyst.

Signal amplification reagents can be attached to the nucleic acids by a variety of linking agents including glutaraldehyde, N,N'-o-phenylenedimaleimide,N,N'-oxydimethylenedimaleimide,N-succinimidyl-4-(N-maleimidomethyl)cyclohexane-1-carboxylate,N-succinimidyl-m-maleimidobenzoate, and N-succinimidyl-3-(2-pyridyldithio)propionate. Signal amplification reagents can include enzymes, metal particles, latex particles, multiple copies of an enzyme or multiple enzymes, highly branched nucleic acids or other similar compounds which can be specifically attached to a secondary probe. These reagents should be selected to specifically enhance the mass of the immobilized target while not disrupting the thin film effect. While the packing of the molecules in the layer do not approach a true thin film, due to the percent occupancy of all available binding sites, they must not disrupt the thin film effect in order to maximize the quality of the generated signal. Thus, amplification reagents cannot behave as discrete particles on the surface of the optical substrate.

After the sample is contacted with the surface of a test device, an instrument can be used to detect analyte binding. One such instrument is the Sagax Ellipsometer (see, U.S. Pat. Nos. 4,332,476, 4,655,595, and 4,647,207 which disclosures are incorporated in full herein and made a part hereof). Alternate instruments suited to this technology include traditional null ellipsometers, thin film analyzers, profilometers, polarimeter, etc. If the interference film is included in the test surface construction, then a simple reflectometer is adequate for quantitation. Unlike conventional ellipsometry, the Comparison Ellipsometer is designed to allow broad field measurements. This feature allows simultaneous measurement of the entire reaction zone. Therefore, measurement errors do not arise because of non-homogeneous binding or reaction patterns.

For the analysis of specific binding reactions on a test surface, a number of modifications greatly improve the performance of the Comparison Ellipsometer. The original design relied on the observer's eye for inspection of the surface.

A detector may be mounted where the eyepiece is located in the original instrument. It may also be mounted at 90° to the side of the light path by incorporation of a partially silvered mirror or beamsplitter set at 45° to reflect a portion of light to a detector, and the rest to the eyepiece for visual alignment of samples. If the mirror is inserted into the optical path, the spot intensity reaching the detector will be only a fraction of the light available. If the detector is directly in the optical pathway without a mirror, 100% of the sample intensity reaches the detector. When a beamsplitter and eyepiece are included in the apparatus, if care is not taken, stray light can be introduced which degrades the optical signal incident on the detector.

A photodiode array may be programmed to dedicate individual photodiodes to measure the intensity of reaction zones or spots, while other photodiode arrays measure the background, or control zones. Simultaneous measurement of the spot intensity and the background intensity allows each reading to be accurately corrected for test surface background.

Either a linear array or a matrix array may be used. A linear array may only measure along one, pre-set axis of the sample spot depending on the size and resolution available in the arrays. The matrix array could measure the entire reacted spot plus background.

The instrument may also be modified to include a variable magnification function or a zoom to allow different spots to fill the photodiode without capturing any background signal. A semi-reflective mirror was introduced between the zoom and the ocular at 45°. Within the ocular, suitably positioned in the middle of the field and in focus was set a reticle of an ellipse. The reticle was selected to match an average sample spot size. On the optical path center line, reflected 90° from the principal axis, was set a mask which matches the size of the reticle. The distance from the center of the mirror to the reticle is the same as from the center of the mirror to the mask. The mirror was mounted by adjusting screws so that the image seen within the reticle would be identical to the image appearing within the mask. Behind the mask, a distance of a few millimeters, was mounted a photosensitive cell arranged to only read the light which passes through the mask and therefore from the selected image. The semi-reflective mirror is of a thickness such that a secondary image appears from the second surface. This is eliminated by using a suitably coated thin mylar membrane as the beamsplitter.

A constant light source, white light or mono-chromatic, is provided by using a power supply that has feedback capabilities. A photoresistor is mounted inside the original instrument's lamp house/heat sink which monitors the light output of the lamp. If the light output changes a corresponding resistance change occurs, thereby affecting the current/voltage sent to the lamp.

The power supply is set to deliver +15 $V_{DC}$ to the lamp while the photoresistor is disconnected. When the photoresistor is connected, it maintains the light output at the level that is produced with a +15V source. A constant light source is required if the instrument is to be used for quantitation. The instrument may also be modified with a BNC port that will enable the output of the photodiode detector amplifier to output to an A/D converter board in a computer or other dedicated device. The dedicated device or computer reads the input signal, designates/names and stores the input, manipulates the, named input, i.e., conducts statistical analyses, e.g., and prints the input data and any other desired calculations derived from the input.

The reflectometer is a very simple instrument which allows measurement of a color change or a change in intensity. A standard halogen light source is used. This will provide polychromatic light. The light source is positioned relative to the test surface such that the maximum intensity of the incident light impinges the test surface. The detector may be a photomultiplier or the like. The angle with which the light impinges the test surface determines the angle at which the detector is placed relative to that surface.

Another useful instrument is a thin film analyzer which uses a monochromatic light source. If the light is not sufficiently linearly polarized, then a polarizer near the source may be used to polarize the light. The polarizer must be positioned to allow the maximum intensity of light to pass through to the test surface. By off-setting the initial polarizer a component of light polarized perpendicular to the plane of incidence, in addition to the light polarized parallel to the plane, is allowed to interact with the surface. Light impinges the test surface at an angle which is sufficiently removed from Brewster's angle, between 50 and 75 degrees off the normal. The polarizer/detector is set at the same angle from the normal as the incident light source relative to the test surface. The polarizer is set from 20 to 15° above the setting which aligns the polarizers for total extinction of light. Incident angles of 30° to 40° off the normal provide adequate resolution of very dilute samples, but may not provide sufficient range for all applications. The second polarizer, or analyzer polarizer, cannot adequately minimize the background signal when the light is incident on the surface at angles greater than 65°. However, the dynamic range is sufficient to allow for electronic reduction in the background signal. The light is reflected from the test surface through the polarizer/analyzer combination prior to being measured at the detector. The detector may be a single photodiode or a photodiode array. A blank test surface is placed in the sample position and used to align the second polarizer. The second polarizer should be positioned at an angle with respect to the first polarizer such that it is a few degrees off the minimum (maximum extinction of light through to the detector). Thus, the background of the test surface produces a low detectable signal, but the change in light intensity is now a function of the change in thickness.

The thin analyzer eliminates the reference surface requirements of the previous instrument and is easier to reduce in size. The comparison based instruments require that a specific reference surface be designed for each type of test surface to be used. This limits the range of optical substrates and optical thin films which are compatible with a given instrument, unless means for changing the reference surface is provided. This new instrument easily accommodates any combination of thin film and optical substrate using a simple adjustment of the analyzer. The instrument may provide better thickness resolution. This instrument and the modified Comparison Ellipsometer may be powered with a 9V battery or other rechargeable power supply. This prototype supplies an increase in numerical aperture, image brightness and focus. This allows a much higher level of magnification to be used which is important for work with smaller spot sizes. Samples may also be applied much closer to one another than is possible with the Comparison Ellipsometer.

EXAMPLES

Example 1

Evaluation of Attachment Chemistries

A 5'-biotinylated oligonucleotide (capture probe) was used to evaluate attachment chemistries for the immobilization, of DNA capture probes to optically active surfaces. Several attachment or surface chemistries are presented.

Surface 1: T-Polymer

A 128+/−2 Å layer of T-Polymer-Aminoalkyl T-structure branch point polydimethyl siloxane (Petrarch; Bristol, Pa.) was used. A 1:300 (v/v) dilution of the T-Polymer was prepared in 2-methyl-2-butanol. The attachment layer was applied to the silicon wafer by a spin coating method and was cured for 24 hours at 140° C. prior to use. For. spin coating, a 300 µl sample of this solution was placed on a 100 mm virgin test silicon wafer by micropipette, although automated aerosol or spray delivery systems are equally useful, while the wafer was spinning at 7,000 rpm on a photoresist spin-coater.

Surface 2: R-Polymer

A 70+/−2 Å layer of spin on glass was coated onto a virgin silicon wafer as follows. A solution containing 1.6%, each, of trimethyl QAC and octadecyl QAC (quartnery ammonium compound, Petrarch), 36.8% water, 10% methanol, and 50%isopropanol was prepared. A 400 µl sample of this solution was applied to the wafer which was attached to a spin coating apparatus and spinning at 3000 rpm. The wafer is spun until a uniform thin film is generated. The glass is then annealed or cured onto the wafer by incubating for 2 hours at 155° C.

Surface 3: $Si_xN_y$

A 499+/−2 Å layer of silicon nitride was applied to the virgin silicon wafer using standard vapor deposition processes known in the semi-conductor industry.

Surface 4: RT II

A 1:1 mixture of the T-Polymer solution with the R-polymer solution was prepared. A 400 µl sample of this mixture was applied to the wafer which was spinning at 3000 rpm. The wafer was spun until a uniform thin film was generated. The polymer layer is cured onto the wafer by incubating for 2 hours at 155° C.

DNA capture probe was coated onto these wafer surface from a solution containing 50 mM sodium citrate, pH 6.0, 0.1 mg/ml carrier DNA, sheared herring sperm DNA, and 600 µM biotinylated DNA, 26-mer. The probe sequence was 5'CGCTAATATCAGAGAGATAACCCAC-3' (SEQ. ID NO.1). Wafers were incubated in this solution overnight at 4° C. Wafers were removed from the solution and washed with 1× phosphate buffered saline containing 0.2% Tween 20™ detergent (PBS/Tween). The wafers were coated in a BSA (bovine serum albumin) solution for 3 hours at 65° C. There wafers were then rinsed with PBS/Tween detergent.

To measure the amount of biotinylated DNA adsorbed to the surface, the wafers were incubated for 30 minutes with a solution containing streptavidin conjugated to horseradish peroxidase (immunology Products) was diluted 1:250 in 50 mM MOPS, pH 7.0, containing 3% alkaline treated casein, 0.2% TWEEN20 detergent, and 0.5% Proclin 300 (an antibacterial agent). Wafers were then washed with deionized water and dried under a stream of nitrogen. A drop of TMB precipitating substrate was applied to the surface and the wafers incubated for 30 minutes at room temperature. Thickness increases (in Angstroms) due to substrate deposition were measured using an absolute ellipsometer (Gaertner) which was normalized to the initial substrate thickness. See FIG. 1. These experiments were repeated using alkaline phosphatase conjugated to streptavidin and BCIP/nitroblue tatrazolium substrate pair. The R-polymer surface (most polar surface used) and the T-polymer surface (least polar surface used) all performed well. These experiments demonstrate that DNA can be successfully immobilized to the surface of the silicon wafer.

Example 2
Sensitivity Evaluation in an Un-optimized Assay

Figure 2:
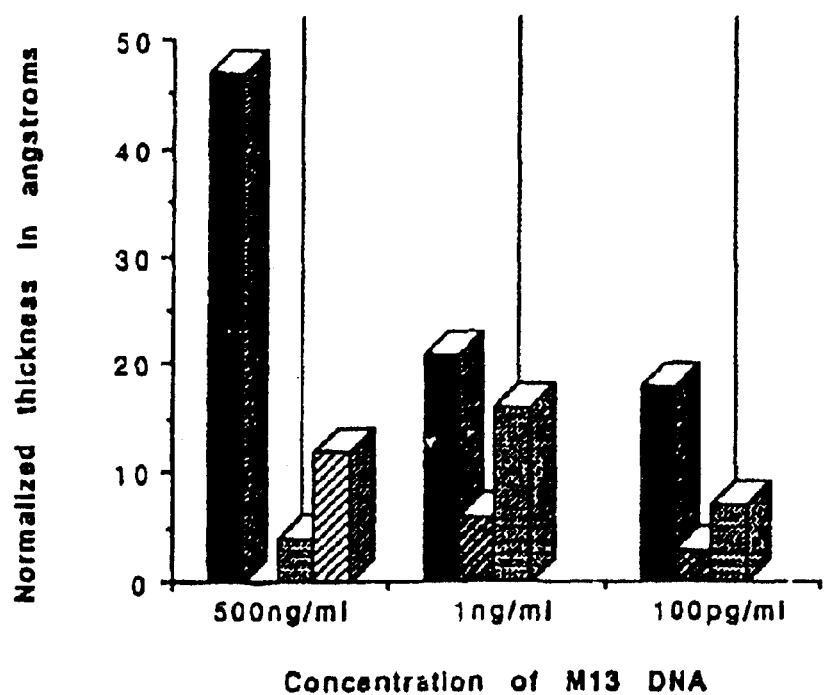
FIG. 2 is a chart comparing the thickness of alkaline phosphatase reaction product on a T-polymer surface with the hybridization concentration of M13mp18 DNA. Solid rectangles represent DNA and conjugate. Darkly stippled rectangles represent conjugate only. Lightly stippled rectangles represent DNA only. Striped rectangles represent no DNA and no conjugate. The y axis represents thickness in angstroms normalized to the substrate thickness. The x axis represents concentrations of M13mp18 DNA in the initial hybridization reaction.

Wafers coated with T-polymer (see Example 1) were coated for 56 hours at 4° C. in a solution containing 50 mM sodium citrate buffer, pH 6.0, 5×SSC, and 20 µg/ml of the ssDNA capture probe complimentary to M13mp18. The probe sequence was CGCTAATATCAGAGAGATAAC-CCAC (SEQ. ID NO. 1). Probe coated wafers were removed from coating solution and placed into a blocking solution containing 5×Denhart's solution, 0.5% SDS, 1 mg/ml carrier DNA, and 25 mM buffer at pH 6.5. They were incubated 16–18 hours at 4° C. and then rinsed with phosphate buffered saline containing 0.0005% TWEEN20 detergent at pH 7.4, Capture probe coated wafers were hybridized with M13mp18 plasmid overnight at 60° C. in a solution containing 1×Denhardt's solution, 0.5% SDS, 25 mM MES, pH 6.5, 0.2 mg/ml carrier DNA, 5×SSC, a final concentration of M13mp18 was 500 ng/ml, 1 ng/ml or 100 pg/ml. The final hybridization step occurred under the same solution and incubation conditions as the previous step with a final biotinylated amplifying probe concentration of 92 µM. The amplifying probe contains strand sequence from 6249 to 6273 and was biotinylated at residue 6261. The sequence is GCAGGTCGACTGTAGCAGGATGCCGG (SEQ. ID NO. 2). All appropriate controls were performed. Wafers were incubated with a steptravidin alkaline phosphatase conjugate. Precipitating substrate, BCIP/nitroblue tetrazolium, was used to generate an increase in thickness at the surface of the wafer. Thickness increases were measured using an absolute ellipsometer (Gaertner). Results for the experiment are shown in FIG. 2. From this experiment, it was concluded that a sensitivity of 1 ng/ml and potentially as low as 100 pg/ml was achieved. This translates to a copy number of roughly 10 10 for a very un-optimized assay.

Example 3
Spin Coating of the DNA Capture Probe Spin coating of the DNA capture probe (M13mp18 fragment 6249–6273) was carried out on two wafer polymer preparations: T-polymer and R-polymer. The wafers were prepared as previously described in Example 1. The DNA capture probe was applied using 400 µl of solution and a speed of 4000 rpm. Three coating solutions were prepared as follows:

High Salt Solution:

5 µl of 10 mg/ml sheared herring sperm DNA
25 µl of 0.50M Pipes pH 7.0 buffer
105 µl of methanol (anhydrous)
315 µl of biotinylated DNA stock (316 µg/ml)
50 µl 20X SSC Medium Salt Solution:

5 µl of 10 mg/ml sheared herring sperm DNA
25 µl of 0.50M Pipes pH 7.0 buffer
105 µl of methanol (anhydrous)
315 µl of biotinylated DNA stock (316 µg/µl)
25 µl 20X SSC
25 µl $H_2O$ No Salt Solution:

5 µl of 10 mg/ml sheared herring sperm DNA
25 µl of 0.50M Pipes pH 7.0 buffer
105 µl of methanol (anhydrous)
315 µl of biotinylated DNA stock (316 µg/ml)
50 µl $H_2O$ After spin coating, the wafers were broken into 6 pieces (chips) and sorted to undergo the following post coating treatments.

1: 60° C., 2 hours

2: 45° C., 2 hours

3: Room temperature, 2 hours

4: 40° C., 4 hours

5: 60° C., 4 hours

6: Room temperature, 4 hours

Figure 3:
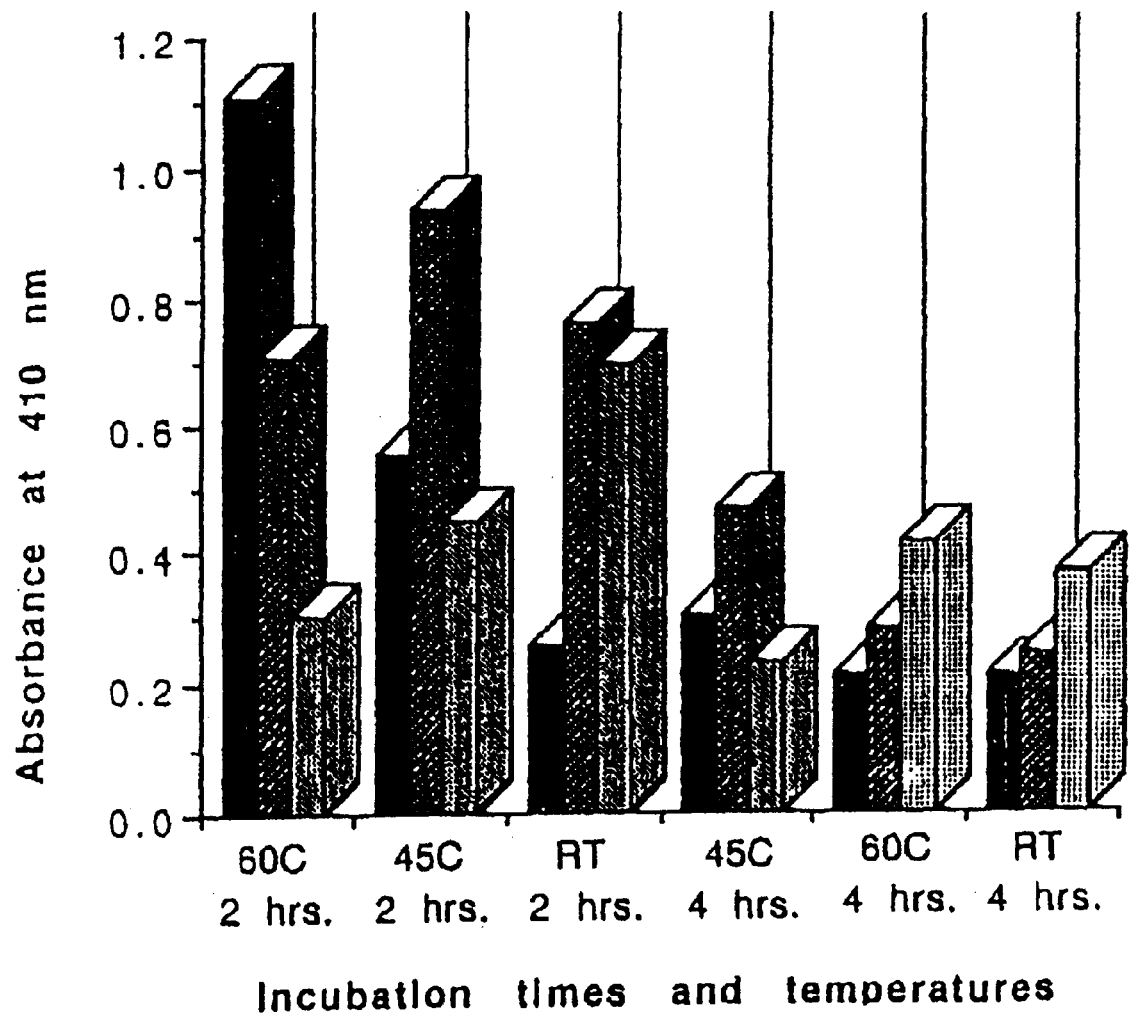
FIG. 3 is a chart comparing the absorbance of substrate at 410 nm with the composition of spin coating solutions of biotinylated DNA coated onto T-polymer surfaces which were subjected to various post coating treatments. Solid rectangles represent no salt in the coating solution. Darkly stippled rectangles represent medium salt concentration in the coating solution. Lightly stippled rectangles represent high salt concentration in the coating solution. The y axis represents absorbance at 410 nm. The x axis represents post coating treatment: incubation times and temperatures.

After the post coating treatment process individual 0.75cm² test surfaces were cut and placed into assay devices. After the wafers were placed in the device they were washed with wash buffer (2×SSC, 0.1% (w/v) SDS) to remove any unbound DNA capture probe. A control wafer for each surface was included. The control did not include a conjugate incubation step and received substrate only. Test wafers were incubated for 15 minutes at room temperature with a 100 µl spot of a 1:1000 dilution of a streptavidin/HRP conjugate. The conjugate was aspirated from the surface and then the surface thoroughly washed with wash buffer. A 100 µl spot of the 2 part Kirkegaard and Perry TMB substrate was applied and incubated at room temperature for 10 minutes. The substrate was quantitatively transferred to a microtiter well containing 100 µl of 2.5M sulfuric acid and then the absorbance measured at 410 nm. Results using the T-polymer are shown in FIG. 3. Solution coating of the DNA capture probe onto the T-Polymer surface provided a functional surface, but only captured approximately ¼ of the probe that the spin coating technique provided. For the solution coating of probe to the surface, the salt concentration of the coating solution was the most critical variable. The optimal coating solution was determined to be 0.25 mg/ml of carrier DNA, 6×SSC pH 7.5, room temperature incubation, and the best surface was the T-Polymer.

Example 4
Adherence of Covalently Bound DNA Under Stringent Conditions

Virgin silicon wafers were coated with a layer of film forming latex consisting of free carboxylic acid groups. A 30% stock solution of TC7A (Seradyn, Indianapolis, Ind.) was diluted to a 0.5% solid in methanol. A 300 microliter sample was applied to the substrate using the spin coating technique and was cured at 37° C. for 120 minutes prior to use. A final thickness of this material is preferred to be 240 Å. These carboxylic acid groups were reacted with NHS (20 mM), N,N'-dicyclohexylcarbodiimide (DCC, 20 mM) in dioxane. These components were mixed on ice for 15 minutes and then incubated for 4–5 hours at room temperature. Then 32 mmoles of hydrazine was added to leave a reactive hydrazide on the surface. The mixture was incubated for 1 hour on ice and then overnight at room temperature. A DNA capture probe with a 3' terminal ribonucleotide residue was treated with sodium periodate at a DNA:NaIO$_4$ ratio of 1:15 for 1 hour to leave a dialdehyde group on the polynucleotide. The dialdehyde then adds to the carbonyl surface to form a covalent adduct of the capture probe on to the surface.

An 18 mer DNA/RNA chimera was utilized as the capture probe. The probe was biotinylated at the 5' end and has a ribonucleotide cytosine on the 3' end. The DNA sequence was 5'-CGAAGCTTGGATCCGCC-3' (ribose) (SEQ. ID No. 3). The covalently attached capture probe was treated with S1 nuclease to degrade the entire probe from the surface. The SI nuclease was mixed in a solution of 0.2 mM NaCl, 0.05 M sodium acetate pH 5.4, 1 mM ZnSO, and 0.5% glycerol to a final concentration of 2 units/ml. A section of the wafer was submerged into 7 ml of the enzyme solution and incubated for 10 minutes at 37° C. Wafers were rinsed prior to enzyme treatment in water for 2 hours at 45° C. The enzyme solution was decanted into test tubes and a small volume of water used to rinse the wafers. The combined solution was dried with a SpeedVac system. The pellet was extracted into acetone and the solution dried. These pellets were re-suspended in 70 µl of water and the A$_{260}$ measured in a microcuvette. The surface density of the probe was determined to be 50 ng/cm$^2$. Control surfaces where no NaIO$_4$ was used, no covalent attachment, did not generate signal. Control surfaces without DNA or without S1 nuclease gave no signal.

Figure 4:
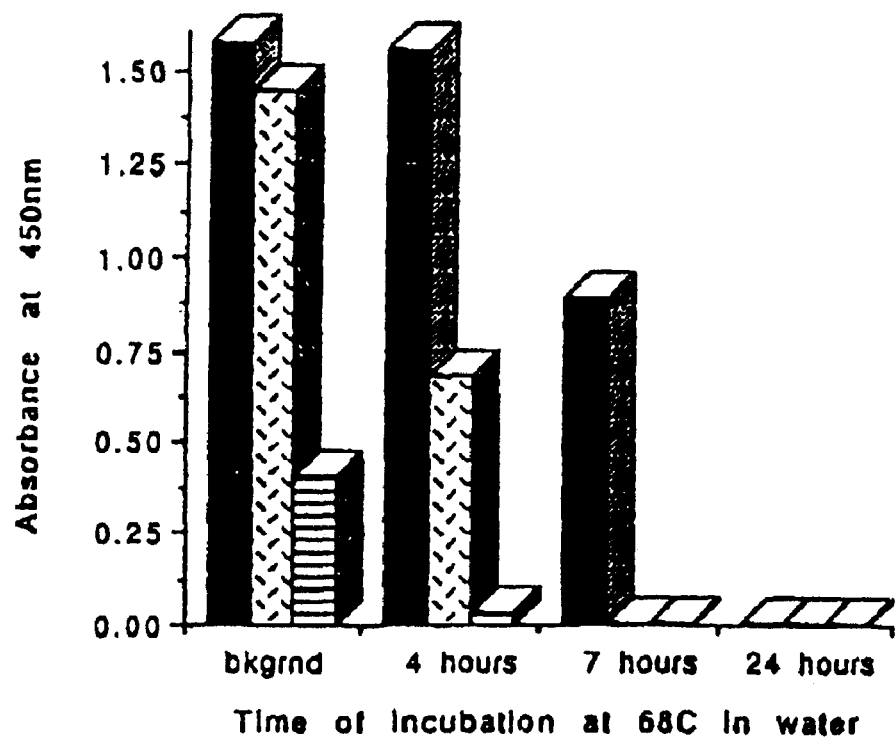
FIG. 4 is a chart comparing the amount of capture probe remaining bound under various stringency conditions. Capture probe was initially covalently bound (solid rectangles); adsorbed (stippled rectangles) or represent non-covalently bound (striped rectangles). The y axis represents absorbance at 450 nm. The x axis represents time of incubation at 68° C. in water.

Wafers with covalently attached capture DNA, probe were incubated at 68° C. in pure water for 4, 7, or 24 hours in order to simulate very extreme conditions of stringency. Wafers were removed, dried and incubated with a streptavidin HRP conjugate. Unbound conjugate was rinsed from the surface. The Kirkegaard and Perry two component TMB substrate was applied for 20 minutes at room temperature. After four hours, the intensity of the ELISA was not changed, indicating that the capture DNA probe on the surface had not been stripped to any significant extent. A wafer with adsorbed, non-covalently bound DNA probe was shown to lose all of its DNA probe under these conditions. See FIG. 4.

Example 5
Estimated Sensitivity Based On Bound Capture Probe

An 8-mer was synthesized and was 5' biotinylated and had a 3' ribose. The DNA sequence was 5'AAAGATGTA (ribose)-3' (SEQ ID NO. 4). The 8-mer was immobilized using the 15:1 periodate:probe ratio to a TC7 coated optical substrate as described in Example 4. Chips were coated at the concentrations listed in the table below. The amount of immobilized biotinylated DNA was measured by reacting a predetermined surface area with a sufficient volume of 1:1000 dilution of a streptavidin/horseradish peroxidase conjugate to cover the test surface. The conjugate and surface were incubated at room temperature for 10 minutes. The chips were rinsed 2 times with wash buffer and then water. The Kirkegaard and Perry two component TMB substrate was applied for 20 minutes at room temperature. A volume of the substrate was placed in a microtiter well with 50 ul of 2.5 N sulfuric acid and 50 ul of water. The absorbance at 450 nm was measured in a microtiter plate reader. The minimum detectable amount of biotinylated DNA was correlated to the copy number of capture probe used in the initial coating solution. The results are shown below:

| CONCENTRATION OF COATING SOL. | COPY # | Ave A$_{450}$ |
|---|---|---|
| 22 µM | 10$^{15}$ | 0.907 |
| 0.22 µM | 10$^{13}$ | 0.808 |
| 0.22 nN | 10$^{10}$ | 0.176 |
| 22 fM | 10$^6$ | 0.175 |
| 0 | 0 | 0.017 |

Assuming a one to one correspondence of binding between capture probe and target sequence, the copy number should represent an estimation of the sensitivity of an unoptimized assay for the detection of target sequence.

Other embodiments are within the following claims.

What is claimed is:

1. A support for detecting the presence of a target nucleic acid in a reflection-based assay comprising an optically smooth, flat, light reflecting surface, said surface having a nucleic acid complementary to said target nucleic acid bound thereto; and said support having a first set of reflective and transmissive properties in response to light impinging thereon and having a second set of reflective and transmissive properties, different from said first set, in response to light when the target nucleic acid is bound to the nucleic acid complementary to said target nucleic acid and creating a change in mass on said optically smooth, flat, light reflecting surface.

2. The support according to claim 1 wherein said nucleic acid bound to said surface is bound by covalent bonding.

3. The support according to claim 1 wherein said support comprises silicon or glass.

4. The support according to claim 1, wherein said light reflecting surface comprises a layer of aluminum or silicon.

5. The support according to claim 4, wherein said layer of aluminum or silicon is a layer of a compound selected from the group consisting of silicon dioxide, silicon monoxide, and aluminum oxide.

6. The support according to claim 5, wherein said support further comprises an anti-reflection layer.

7. The support according to claim 1, wherein said nucleic acid bound to said surface is indirectly bound through an intermediate molecule bound to said surface.

8. The support according to any one of claims 1–7, wherein said support further comprises said target nucleic acid bound to said complementary nucleic acid, wherein reflectance from said light-reflecting surface is altered in comparison to reflectance by said light-reflecting surface in the absence of said bound target nucleic acid.

* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: Bacteriophage M13mp18
<220> FEATURE:
<223> OTHER INFORMATION: Capture probe complimentary to M13mp18

<400> SEQUENCE: 1
cgctaatatc agagagataa cccac                                        25
```

```
-continued

<210> SEQ ID NO 2
<211> LENGTH: 26
<212> TYPE: DNA
<213> ORGANISM: Bacteriophage M13mp18
<220> FEATURE:
<223> OTHER INFORMATION: Amplifying probe complimentary to M13mp18

<400> SEQUENCE: 2
gcaggtcgac tgtagcagga tgccgg                                              26

<210> SEQ ID NO 3
<211> LENGTH: 17
<212> TYPE: DNA
<213> ORGANISM: Bacteriophage M13mp18
<220> FEATURE:
<223> OTHER INFORMATION: 17-mer DNA/RNA chimera

<400> SEQUENCE: 3
cgaagcttgg atccgcc                                                        17

<210> SEQ ID NO 4
<211> LENGTH: 9
<212> TYPE: DNA
<213> ORGANISM: Bacteriophage M13mp18
<220> FEATURE:
<223> OTHER INFORMATION: 9-mer

<400> SEQUENCE: 4 aaagatgta                                                                  9
```